United States Patent
Kremminger et al.

(10) Patent No.: US 9,139,597 B2
(45) Date of Patent: Sep. 22, 2015

(54) METHOD FOR THE PRODUCTION OF CEFTOBIPROLE MEDOCARIL

(75) Inventors: Peter Kremminger, Kundl (AT); Johannes Ludescher, Kundl (AT); Hubert Sturm, Kundl (AT)

(73) Assignee: SANDOZ AG, Basel (CH)

( * ) Notice: Subject to any disclaimer, the term of this patent is extended or adjusted under 35 U.S.C. 154(b) by 708 days.

(21) Appl. No.: 13/320,430

(22) PCT Filed: May 25, 2010

(86) PCT No.: PCT/EP2010/057105
§ 371 (c)(1),
(2), (4) Date: Jan. 20, 2012

(87) PCT Pub. No.: WO2010/136423
PCT Pub. Date: Dec. 2, 2010

(65) Prior Publication Data
US 2012/0108807 A1    May 3, 2012

(30) Foreign Application Priority Data
May 25, 2009   (EP) .................................... 09161028

(51) Int. Cl.
*C07D 501/56*   (2006.01)
*C07D 501/04*   (2006.01)
*C07D 501/18*   (2006.01)

(52) U.S. Cl.
CPC ............ *C07D 501/56* (2013.01); *C07D 501/04* (2013.01); *C07D 501/18* (2013.01)

(58) Field of Classification Search
USPC .................................................. 540/219, 222
See application file for complete search history.

(56) References Cited

U.S. PATENT DOCUMENTS 6,384,214 B1   5/2002   Spurr
6,504,025 B2 *  1/2003   Hebeisen et al. ............. 540/222

FOREIGN PATENT DOCUMENTS

| EP | 0037380 | A2 | 7/1981 |
| EP | 0841339 | A1 | 5/1998 |
| EP | 0849269 | A  | 6/1998 |
| EP | 1067131 | A1 | 10/2001 |
| EP | 1087980 | B  | 1/2003 |
| WO | 9529182 | A  | 11/1995 |
| WO | 9965920 |    | 12/1999 |
| WO | 0104127 |    | 1/2001 |
| WO | 0190111 | A1 | 11/2001 |
| WO | 0214332 |    | 2/2002 |

OTHER PUBLICATIONS

International Search Report and Written Opinion (mailed Jul. 27, 2010).
Van Look, Ger. Silylating Agents, Fluka Chemika AG, Switchzerland. 1995.
Kocienski, Philip J. Protecting Groups 3rd Ed. Thieme. Germany. 2005.
Final Office Action issued in U.S. Appl. No. 13/320,414. Aug. 13, 2013.
Greene, Theodora W. Greene's Protective Groups in Organic Synthesis 4th ed. Ch. 5 and7, John Wiley & Sons, Inc. New Jersey. 2007.
Current Opinion in Pharmacology 2006, 6, 480-485.
J. Antibiotics 37:557-571, 1984.
Yakugaku Zasshi 110 (9) 658-664, 1990.
Fluka, 1995, Fluka Chemi AG, CH-9471, Switzerland, pp. 1-45.

* cited by examiner

*Primary Examiner* — Golam M M Shameem
*Assistant Examiner* — Laura Daniel
(74) *Attorney, Agent, or Firm* — Jeffrey S. Melcher; Manell Selter PLLC

(57) ABSTRACT

The present invention relates to a method for the production of organic compounds, in particular sodium (6R,7R)-7-[(Z)-2-(5-amino-[1,2,4]thiadiazol-3-yl)-2-hydroxyimino-acetylamino]-8-oxo-3-[(E)-(R)-1'-(5-methyl-2-oxo-[1,3]-dioxol-4-ylmethoxycarbonyl)-2-oxo-[1,3']bipyrrolidinyl-3-ylidenemethyl]-5-thia-1-aza-bicyclo[4.2.0]oct-2-ene-2-carboxylate (ceftobiprole medocaril), and compounds of the general formula (1) and of the general formula (2), the compounds themselves and intermediates in the production according to the invention.

10 Claims, No Drawings

METHOD FOR THE PRODUCTION OF CEFTOBIPROLE MEDOCARIL

CROSS-REFERENCE TO RELATED APPLICATIONS

This application is a national stage entry under 35 U.S.C. 371 of International Application No. PCT/EP2010/057105, filed 25 May 2010, designating the United States. This application claims foreign priority under 35 U.S.C. 119 and 365 to European Patent Application No. 09161028.7, filed 25 May 2009.

The present invention relates to a method for the production of organic compounds, in particular sodium (6R,7R)-7-[(Z)-2-(5-amino-[1,2,4]thiadiazol-3-yl)-2-hydroxyimino-acetylamino]-8-oxo-3-[(E)-(R)-1'-(5-methyl-2-oxo-[1,3]-dioxol-4-ylmethoxycarbonyl)-2-oxo-[1,3']bipyrrolidinyl-3-ylidenemethyl]-5-thia-1-aza-bicyclo[4.2.0]oct-2-ene-2-carboxylate (ceftobiprole medocaril), and compounds of the general formula (1) and of the general formula (2), the compounds themselves and intermediates in the production according to the invention. Ceftobiprole medocaril is a parenteral cephalosporin with outstanding antibacterial properties. An overview is given in, for example, Current Opinion in Pharmacology 2006, 6, 480-485.

Methods for the production of ceftobiprole medocaril are known per se. The methods known from the prior art have the common feature that starting from 7-aminocephalosporanic acid, a large number of intermediate stages have to be isolated and purified in order to obtain ceftobiprole medocaril of the general formula (1) in a sufficient purity.

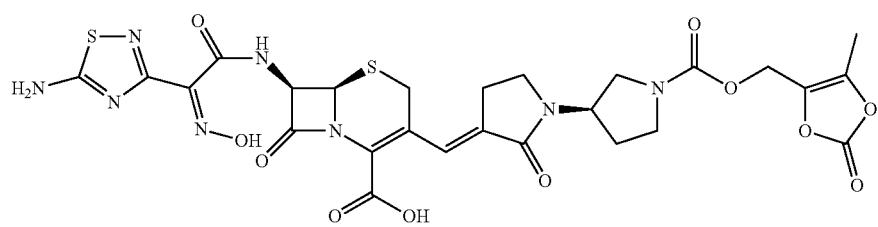

(1)

The compound of the general formula (1) is known per se and is described, for example, in WO 99/65920. It can be used for treatment and for prophylaxis of bacterial infectious diseases, in particular infectious diseases which are caused by methicillin-resistant *Staphylococcus aureus* strains.

WO 99/65920 describes, as the last step of the production process of ceftobiprole medocaril, a reaction in which the medocaril prodrug unit is introduced into a compound of the general formula (2).

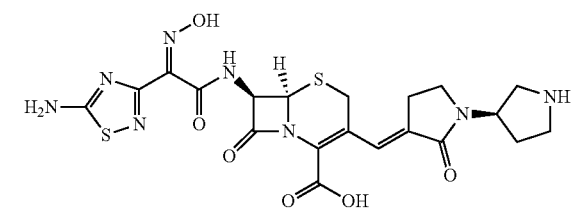

(2)

The compound of the general formula (2) is likewise known per se and has been described, for example, in EP 0 849 269 A1. According to EP 0 849 269 A1, the production of the compound of the general formula (2) is carried out starting from (2R,6R,7R)-tert-butoxycabonylamino-3-formyl-8-oxo-5-thia-1-azabicyclo[4.2.0]oct-3-ene-2-carboxylic acid benzhydryl ester by a Wittig reaction with (1'-allyloxycarbonyl-2-oxo-[1,3']bipyrrolidinyl-3-yl)-triphenylphosphonium bromide. The Δ2 reaction product formed in this reaction is isomerized back into the desired Δ3 isomer by sulfoxidation and subsequent reduction, and thereafter deprotected from the benzhydryl ester with trifluoroacetic acid. The acylation in position 7 is carried out by reaction with (Z)-(5-amino-[1,2,4]-thiadiazol-3-yl)-trityloxyiminothioacetic acid S-benzothiazol-2-yl ester. The compound of the general formula (2) is subsequently obtained by splitting off the protective groups.

EP 1 067 131 A1 describes the formation of the ylide in toluene or a mixture of toluene and methylene chloride by addition of alkali metal tert-butylate in tetrahydrofuran, by which means the base can be added as a solution. The reaction of the ylide with the corresponding aldehyde at a reaction temperature of −70° C. is described.

EP 0 841 339 A1 relates to cephalosporin derivatives and methods for the production thereof. WO 95/29182 likewise discloses intermediate products for the production of cephalosporins.

WO 01/90111 describes a further production of ceftobiprole medocaril in several stages starting from deacetyl-7-aminocephalosporanic acid by acylation with (Z)-(5-amino-[1,2,4]-thiadiazol-3-yl)-trityloxyiminothioacetic acid S-benzothiazol-2-yl ester in N,N-dimethylformamide, followed by in situ esterification with diphenyldiazomethane in methylene chloride to give the corresponding benzhydryl ester, which is precipitated by addition of hexane and isolated. In the next step, this product is oxidized with TEMPO/NaOCl in methylene chloride/water or with manganese dioxide in tetrahydrofuran/methylene chloride to give the corresponding aldehyde. The next reaction step comprises the Wittig reaction to give the 3-vinyl-substituted derivative, in which the reaction is carried out in methylene chloride/toluene/tetrahydrofuran at −78° C. The crude product is extracted by stirring with ethanol and recrystallized from methylene chloride/tert-butyl methyl ether or purified by chromatography. According to the method disclosed in WO 01/90111, the Wittig reaction is carried out at low temperatures of from −80 to −70° C. in a complex solvent mixture of methylene chloride, toluene and tetrahydrofuran. When the reaction is carried out on a production scale, this leads to considerable disadvantages, since regeneration of the process solvents is made difficult.

A disadvantage of the syntheses known from the prior art is that the compound of the general formula (2) or of the general formula (1) is produced via a multi-stage process which comprises complex synthesis steps and delivers poor overall yields. Furthermore, involved protective group operations groups are necessary.

It has now been found, surprisingly, that compounds of the general formula (1) and of the general formula (2) can be produced via a method which can be carried out with few stages, even on an industrial scale.

Unless explicitly stated, the following statements in the context of the present invention in each case relate to the said compounds themselves and pharmaceutically acceptable salts thereof.

The present invention accordingly relates to a method for the production of a compound of the general formula (1)

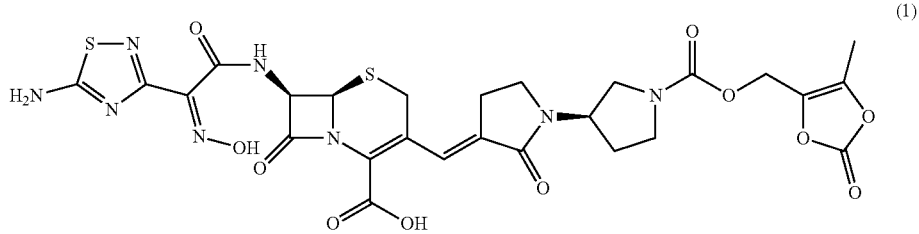

(1)

comprising at least the following steps (a), (b) and (c):

(a) reaction of a compound of the general formula (3)

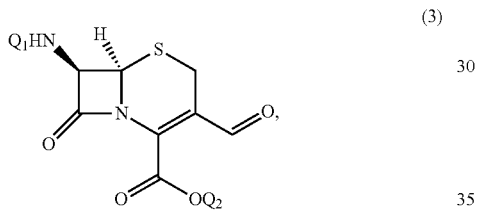

(3)

wherein $Q_1$ and $Q_2$ independently of each other represents a hydrogen atom or a silyl group, with a compound of the general formula (4)

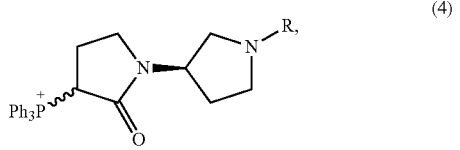

(4)

wherein R represents an amino-protective group, to give a compound of the general formula (5)

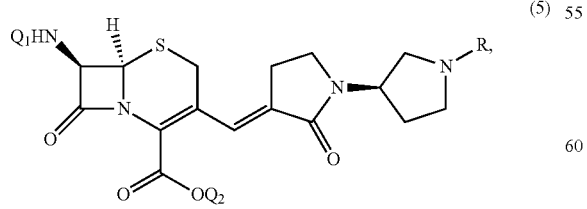

(5)

wherein $Q_1$, $Q_2$ and R are as defined above;

(b) reaction of the compound of the general formula (5) with a compound of the general formula (6)

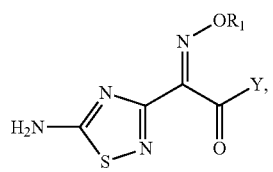

(6)

wherein $R_1$ represents a hydroxy-protective group and Y represents an activating functionality, where appropriate after removal of the protective group, if $Q_1$ represents a silyl group, to give a compound of the general formula (7)

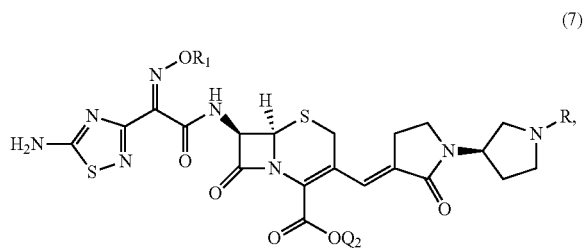

(7)

wherein $R_1$, $Q_2$ and R are as defined above;

(c) conversion of the compound of the general formula (7) into the compound of the general formula (2), where appropriate after removal of the protective group, if $Q_2$ represents a silyl group,

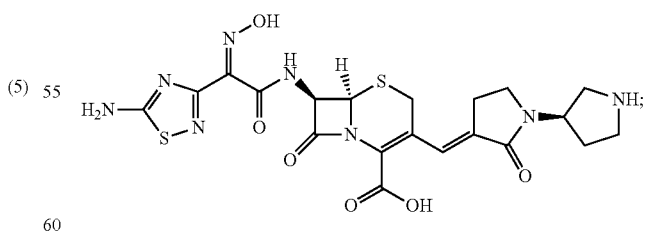

(2)

and optionally (d) conversion of the compound of the general formula (2) into a compound of the general formula (1).

The present invention moreover relates to a method for the production of a compound of the general formula (2)

(2)

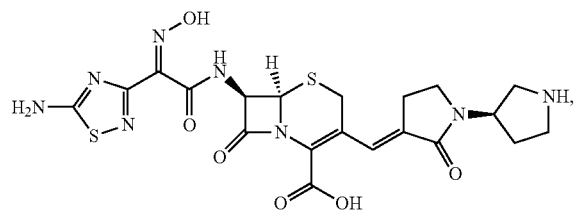

comprising at least the following steps (a), (b) and (c):
(a) reaction of a compound of the general formula (3)

(3)

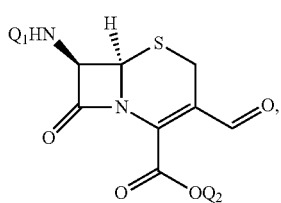

wherein $Q_1$ and $Q_2$ independently of each other represents a hydrogen atom or a silyl group,
with a compound of the general formula (4)

(4)

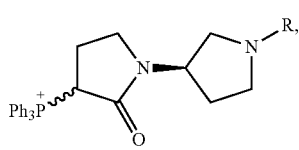

wherein R represents an amino-protective group,
to give a compound of the general formula (5)

(5)

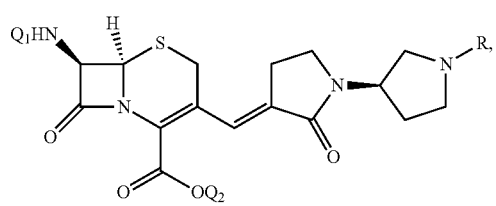

wherein $Q_1$, $Q_2$ and R are as defined above;
(b) reaction of the compound of the general formula (5) with a compound of the general formula (6)

(6)

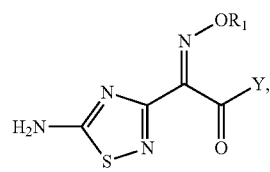

wherein $R_1$ represents a hydroxy-protective group and Y represents an activating functionality,
where appropriate after removal of the protective group, if $Q_1$ represents a silyl group, to give a compound of the general formula (7)

(7)

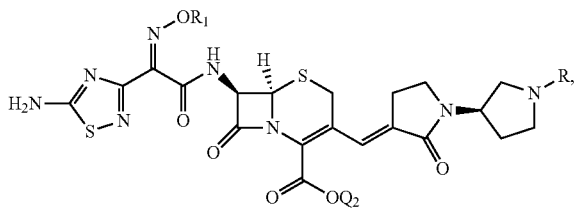

wherein $R_1$, $Q_2$ and R are as defined above;
and
(c) conversion of the compound of the general formula (7) into the compound of the general formula (2), where appropriate after removal of the protective group, if $Q_2$ represents a silyl group.

The methods according to the invention include at least steps (a), (b) and optionally (c). The methods according to the invention can moreover also include further steps, for example protective group operations. In this context, it is possible according to the invention for these further steps to be carried out before or after steps (a), (b) and (c). It is likewise possible, however; for the further steps to be carried out between steps (a) and (b) or between steps (b) and (c).

The method according to the invention makes possible the production of the compound of the general formula (1) or of the general formula (2) in a simple manner and in a high purity.

The method according to the invention includes step (a), i.e. the reaction of a compound of the general formula (3)

(3)

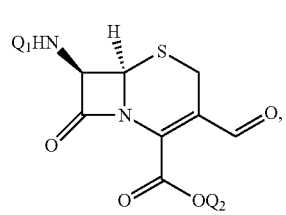

wherein $Q_1$ and $Q_2$ independently of each other represents a hydrogen atom or a silyl group, in particular wherein Q1 and Q2 independently of each other represent a silyl group or wherein Q1 represents a hydrogen atom and Q2 represents a silyl group,
with a compound of the general formula (4)

(4)

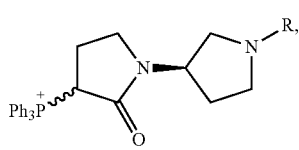

wherein R represents an amino-protective group,
to give a compound of the general formula (5)

(5)

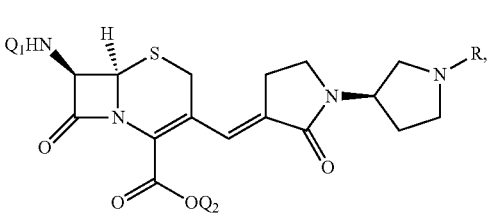

wherein $Q_1$, $Q_2$ and R are as defined above.

According to the invention, the reaction according to step (a) can be carried out in any manner known to the person skilled in the art. In this reaction, the compound of the general formula (3) is reacted with the phosphonium salt of the general formula (4). The reaction is carried out according to the invention in the presence of a base, with the formation of the compound of the general formula (5).

Suitable reaction conditions and solvent systems are described, for example, in WO 95/29182 on page 26, second paragraph to page 27, to the last-but-one paragraph inclusive, and in Example 31 on page 42 in WO 95/29182.

The reaction according to step (a) can be carried out according to the invention, for example, in the presence of a silylating agent and/or an epoxide, in particular in the presence of BSA and/or propylene oxide.

The present invention therefore also relates to a method for the production of a compound of the general formula (1) or a method for the production of a compound of the general formula (2) as described above, wherein step (a) is carried out in the presence of a silylating agent and an epoxide.

According to preferred embodiments, the present invention also relates to a method for the production of a compound of the general formula (1) or a method for the production of a compound of the general formula (2) as described above, wherein the silylating agent is BSA or wherein the epoxide is propylene oxide.

The methods according to the invention moreover include a step (b), i.e. the reaction of the compound of the general formula (5) with a compound of the general formula (6)

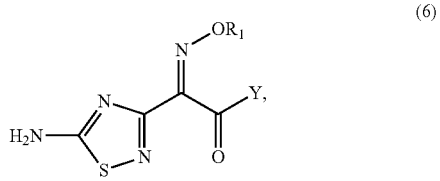
(6)

wherein $R_1$ represents a hydroxy-protective group and Y represents an activating functionality,
where appropriate after removal of the protective group, if $Q_1$ represents a silyl group,
to give a compound of the general formula (7)

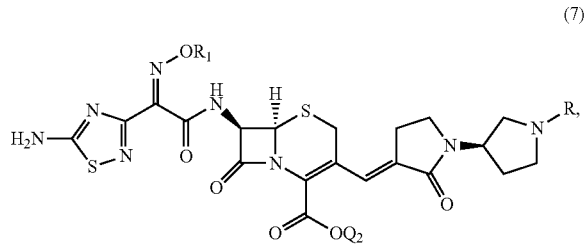
(7)

wherein $R_1$, $Q_2$ and R are as defined above.

According to step (b) of the method according to the invention, the compound of the general formula (5) is acylated with the compound of the general formula (6).

According to the invention, Y is an activating functionality, such as, for example, a halide, suitable halides being disclosed, for example, in J. Antibiotics 37:557-571, 1984, a mixed anhydride, suitable mixed anhydrides being disclosed, for example, in Yakugaku Zasshi 110 (9) 658-664, 1990, or a group chosen from the groups (s), (t) and (u):

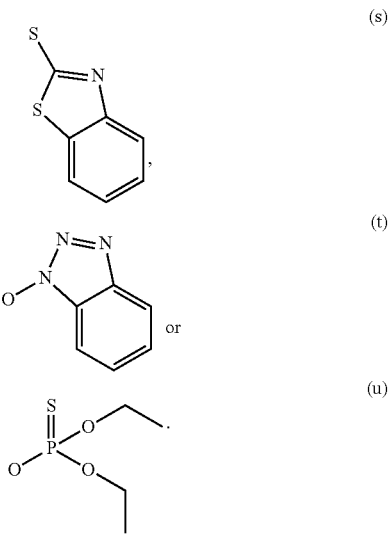

In this context, the reaction according to step (b) of the method according to the invention can in principle be carried out in any manner known to the person skilled in the art.

Suitable reaction conditions and solvent systems are described, for example, in EP 37380 A2 from page 8, line 16 to page 9, line 5.

According to the invention, it is preferable, for the reaction according to step (b), for the compound of the general formula (5) to be dissolved by silylation or salt formation and, after the acylation with the compound of the general formula (6) has been carried out, for the protective groups to be split off in one step.

In this case, in the context of the present invention step (b) can be carried out without intermediate isolation or in a one-pot process.

According to a preferred embodiment, the present invention therefore also relates to a method for the production of a compound of the general formula (1) or a method for the production of a compound of the general formula (2) as described above, wherein for the reaction according to step (b), the compound of the general formula (5) is dissolved by silylation or salt formation and, after acylation with the compound of the general formula (6) has been carried out, the protective groups are split off in one step.

The method according to the invention can also additionally include a step (c), in addition to steps (a) and (b). According to step (c), the conversion of the compound of the general formula (7) into the compound of the general formula (2) is carried out, where appropriate after removal of the protective group, if $Q_2$ represents a silyl group.

Suitable reaction conditions and solvent systems are described, for example, in WO01/90111 on page 11, lines to 27, in particular in Example 5 and 6 of WO01/90111.

According to the invention, it is preferable for step (c) to be carried out without intermediate isolation or in a one-pot process. According to a further embodiment, the present invention therefore also relates to a method for the production of a compound of the general formula (1) or a method for the production of a compound of the general formula (2) as described above, wherein step (c) is carried out without intermediate isolation of the intermediate obtained from step (b) or in a one-pot process.

It has been found, surprisingly, that by means of this method according to the invention a reduction in the number of intermediate stages isolated can be obtained in the production of compound of the general formula (1) or of the general formula (2), in particular of ceftobiprole medocaril, which in the end leads to higher overall yields and as a consequence more favorable production costs.

The method according to the invention for the production of the compound of the general formula (1) preferably also includes, in addition to steps (a), (b) and (c), a step (d), wherein step (d) is carried out after steps (a), (b) and (c). According to the invention, however, it is possible for further steps, for example protective group operations, to be carried out between steps (c) and (d). According to step (d), a Conversion of the compound of the general formula (2) into a compound of the general formula (1) is carried out.

In this context, the conversion according to step (d) of the method according to the invention can in principle be carried out in any manner known to the person skilled in the art.

Suitable reaction conditions and solvent systems are described, for example, in WO99/65920 in Example 1.1 on pages 9 and 10.

The compounds obtained by the method according to the invention are distinguished, inter alia, by a high purity.

According to a further aspect, the present invention also relates to a compound of the general formula (1)

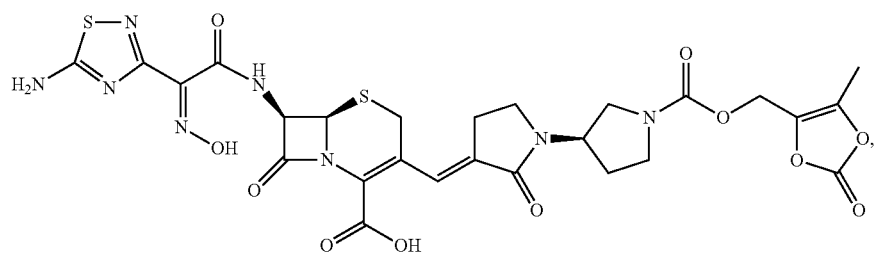

(1)

wherein the compound is obtainable by a method as described above.

The present invention also relates to a compound of the general formula (2)

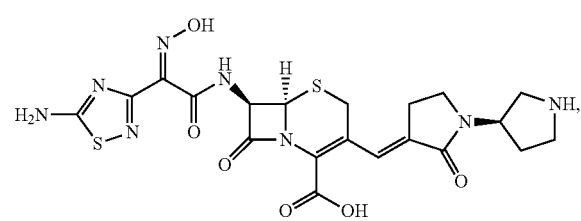

(2)

and salts thereof, in particular salts with strong organic acids, such as the trifluoroacetic acid salt or the tosylate or mesylate, wherein the compound is obtainable by a method as described above or in the examples.

The compound of the general formula (2) is obtained by the method according to the invention in a high purity, for example >99 area percent, for example in a purity of 99.5 area %, determined by means of HPLC, so that the compound of the general formula (1) is obtainable therefrom in a quality which can be employed pharmaceutically without a further purification step.

The present invention also relates to novel intermediates of the synthesis. According to a further aspect, the present invention thus relates to a compound of the general formula (5)

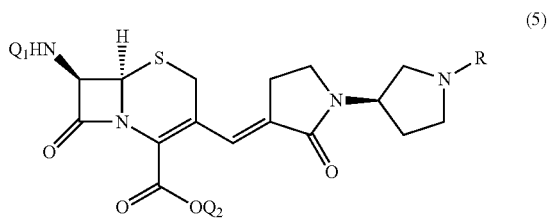

(5)

and salts thereof, in particular organic amine salts, such as e.g. the dicyclohexylamine salt from Example 3, wherein $Q_1$ and $Q_2$ independently of each other represents a hydrogen atom or a silyl group and R represents an amino-protective group, excluding an Alloc group.

All the conventional protective groups, excluding an Alloc group, are suitable according to the invention as the amino-protective group. For example, R represents a BOC group. According to a further embodiment, the present invention accordingly relates to a compound of the general formula (5) as described above, wherein $Q_1$ represents a trimethylsilyl group and R represents a BOC group.

This BOC-protected intermediate crystallizes and is then obtained in a very pure form, for example 99% area percent HPLC or purer. A further essential advantage of the use of the BOC-protected intermediate in the production of ceftobiprole medocaril is that by the method disclosed, the protective groups employed, BOC- and triphenylmethyl-, can be split off simultaneously in step (c), while intermediates described in EP 0849 269 are ALLOC-protected, so that the protective groups must be split off in separate steps. The present invention therefore also relates to the use of this BOC-protected intermediate, that is to say a compound of the general formula (5) as described above, wherein $Q_1$ represents a trimethylsilyl group and R represents a BOC group, in the production of ceftobiprole medocaril.

The present invention also relates to compounds of the general formula (5) or of the general formula (7) obtainable by a reaction according to one of steps (a) or (b) as described above.

The compound of the general formula (5) is an essential intermediate stage of the method according to the invention and makes possible the simple synthesis sequence of the method according to the invention.

The present invention therefore also relates to the use of a compound of the general formula (5) as described above for the production of a compound of the general formula (1) or of the general formula (2). The present invention moreover also relates to the use of a compound of the general formula (5) as described above for the production of a compound of the general formula (1).

The present invention is explained in more detail in the following with the aid of examples.

EXAMPLES

1. Example (6R,7R)-7-Amino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid

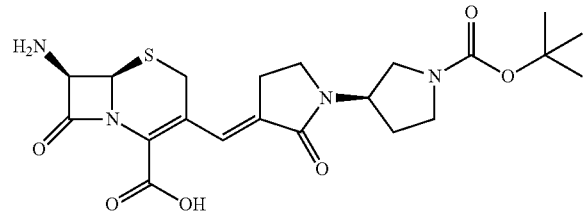 [SMILES: CC(C)(C)OC(=O)N1CC[C@@H](N2CC/C(=C\C3=C(C(=O)O)N4C(=O)[C@@H](N)[C@H]4SC3)C2=O)C1]

5.14 g of 7-amino-3-formyl-ceph-3-em-4-carboxylate were dissolved in 27.8 ml of bis(trimethylsilyl)-acetamide and 50 ml of propylene oxide. 16.8 g of (1R/S,3'R)-(1'-tert-butyloxycarbonyl-2-oxo-[1,3']pipyrrolidinyl-3-yl)-triphenylphosphonium bromide (EP1067131, WO02/14332) were then metered in slowly in portions at 1° C. The mixture was subsequently stirred at 1° C. until the starting material has reacted, and thereafter the crystalline precipitate was filtered off under a nitrogen atmosphere and washed with 50 ml of cyclohexane/bis(tirmethylsilyl)acetamide 99.5/0.5. After drying in vacuo, the desired product was obtained in a silylated form.

The material was dissolved in 100 ml of methylene chloride and 50 ml of 3% strength NaHCO$_3$ solution was added at 0° C. The phases were separated, the organic phase was washed with 30 ml of water and, after treatment with active charcoal, the combined aqueous phases were brought to pH 3.5 with 3% strength H$_3$PO$_4$. The crystalline precipitate was filtered, washed with water and dried in vacuo.

Weight: 6.09 g $^1$H-nmr (DMSO-d$_6$) δ 1.39 (s, 9H), 2.00 (m, 2H), 2.8-3.2 (m, 2H), 3.2-3.5 (m, 6H), 3.84 (ABq, 2H, J=18.2 Hz), 4.57 (m, 1H), 4.82 (d, 1H, J=5.1 Hz), 5.01 (d, 1H, J=5.1 Hz), 7.21 (m, 1H)

$^{13}$C-nmr (DMSO-d$_6$) δ 24.63, 26.11, 28.09, 28.89, 41.54, 44.94, 45.31, 47.98, 48.34, 51.27, 52.00, 58.98, 63.76, 79.95, 121.95, 126.19, 126.28, 129.90, 134.21, 154.97, 164.36, 169.05, 169.13

MS-ESI negative mode: 927.2 (2M-H, 100%, 463.1 (M-H, 25%)

H$_2$O content: 2.2%

IR (golden gate, cm$^{-1}$): 2978, 1793, 1682, 1551, 1397, 1363, 1330

2. Example (6R,7R)-7-Trimethylsilylamino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid trimethylsilyl ester

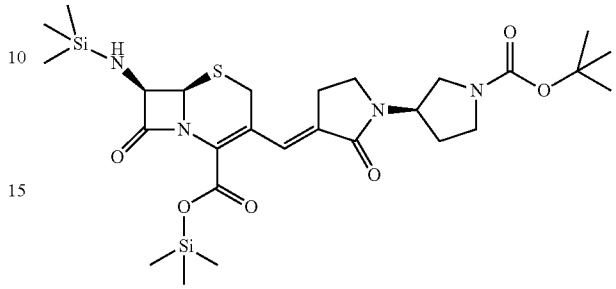

10.28 g of 7-amino-3-formyl-ceph-3-em-4-carboxylate were dissolved in 55.6 ml of bis(trimethylsilyl)acetamide and 100 ml of propylene oxide. 33.6 g of (1R/S,3'R)-(1'-tert-butyloxycarbonyl-2-oxo-[1,3']bipyrrolidinyl-3-yl)-triphenylphosphonium bromide (EP1067131, WO02/14332) were then metered in slowly in portions at 0° C. over 22 h. The mixture was subsequently stirred at 1° C. until the starting material has reacted, and thereafter the reaction mixture was cooled to −20° C. The crystalline precipitate was filtered off under a nitrogen atmosphere and washed with 180 ml of cyclohexane/bis(trimethylsilyl)acetamide 99.5/0.5 in portions. After drying in vacuo, the bis-silylated product was obtained.

Weight: 16.2 g $^1$H-nmr (CDCl$_3$) δ 0.04, 0.10, 0.12 (3s, 9H), 0.34 (s, 9H), 1.43 (s, 9H), 1.74 (br s, 1H), 1.9-2.2 (m, 2H), 2.8-3.0 (m, 2H), 3.2-3.7 (m, 8H), 4.7-4.95 (m, 3H), 7.43 (m, 1H)

3. Example

Dicyclohexylammonium (6R,7R)-7-amino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylate

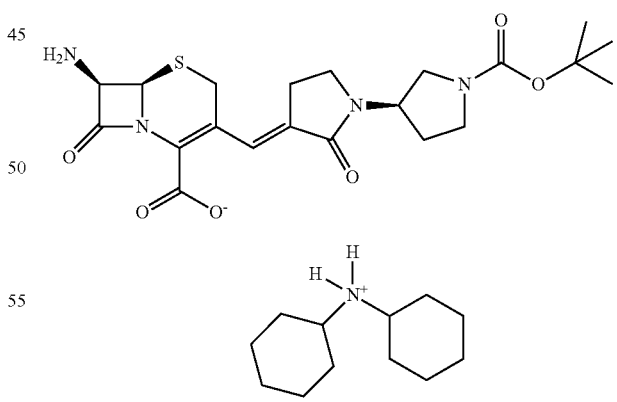

1.0 g of (6R,7R)-7-trimethylsilylamino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid trimethylsilyl ester was dissolved in 10 ml of methylene chloride and a solution of 300 mg of dicyclohexylamine in 1 ml of EtOH and 10 ml of ethyl acetate was added. The precipitate was filtered off, washed with ethyl acetate and dried in vacuo.

Weight: 0.9 g $^1$H-nmr (D$_2$O/DMSO-d$_6$) δ 0.9-1.3 (m, 10H), 1.30 (s, 9H), 1.4-2.18 m, 12H), 2.7-3.5 (m, 10H), 3.64 (ABq, J=17.2 Hz, 2H), 4.5 (m, 1H)*, 4.58 (d, 1H, J=5.1 Hz); 4.88 (d, 1H, J=5.1 Hz), 7.07 (s, 1H)

* tlw. overlapped by D$_2$O signal

MS-ESI negative mode: 927.2 (2M-H, 100%), 463.1 (M-H, 25%)

IR (golden gate, cm$^{-1}$): 2932, 2856, 1754, 1692, 1671, 1630, 1569, 1394, 1329

4. Example (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid trifluoroacetate

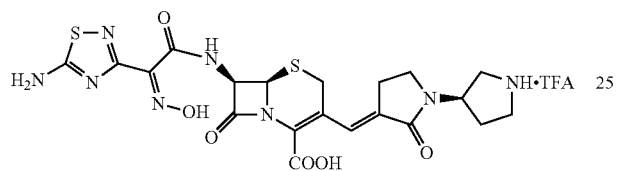

4.1 Variant A:

3.0 g of (6R,7R)-7-amino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid in silylated form were dissolved in 150 ml of methylene chloride at 0°. 600 μl of DMF/water 5/1 and 1.8 ml of bis(trimethylsilyl)acetamide were then added and 2.29 g of 2-trityloxyimino-2-(5-amino-1,2,4-thiadiazol-3-yl)-acetic acid chloride hydrochloride (J. Antibiotics 37:557-571, 1984) were metered into the mixture in portions. After 3 h at 0°, the mixture was poured onto 30 ml of MeOH/120 ml of water and the methylene chloride phase was separated off. The organic phase was concentrated to 66 g and 25 ml of trifluoroacetic acid were added. After 10 minutes, 1.5 ml of triethylsilane and 10 ml of water were added and the mixture was cooled to −15° C. The organic phase was separated off and washed once more with 6 ml of trifluoroacetic acid/water 1/1. The combined aqueous phases were diluted to 150 ml with water and filtered over an adsorber resin column with XAD-1600. After washing out the column with water, it was eluted with water/acetonitrile 85/15. The product-containing fractions was concentrated in vacuo and the residue was left to stand at 0° for after-crystallization. The crystalline product was filtered off, washed with water and dried in vacuo.

Weight: 2.66 g 4.2 Variant B:

7.4 g of (6R,7R)-7-amino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid were dissolved in 781 ml of methylene chloride at 0° with the addition of 6.7 ml of triethylamine. 8.65 g of 2-trityloxyimino-2-(5-amino-1,2,4-thiadiazol-3-yl)-acetic acid chloride hydrochloride were then metered into the mixture in portions. After the starting material had reacted, the mixture was poured onto 500 ml of water and the methylene chloride phase was separated off. The organic phase was dried over Na$_2$SO$_4$ and concentrated in vacuo.

The residue was dissolved in 148 ml of methylene chloride, and 4.5 ml of triethylsilane and 74 ml of trifluoroacetic acid were added at room temperature. After 30 minutes, 222 ml of methylene chloride and 222 ml of water were added and the mixture was cooled to −20° C. The organic phase was separated off and washed once more with a mixture of 37 ml of trifluoroacetic and 148 ml of water. The combined aqueous phases were diluted to 364 ml with water, filtered over an adsorber resin and eluted with acetonitrile/water 15/85. The filtrate concentrated to 35 g on a Rotavapor and filtered and the residue was washed with water. After drying in vacuo, a weight of 4.5 g was obtained.

$^1$H-nmr (DMSO-d$_6$) δ 1.9-2.2 (m, 2H), 2.8-3.5 (m, 8H), 3.85 (Abq, 2H; J=18.3 Hz), 4.63 (m, 1H), 5.16 (d, 2H, J=4.9 Hz), 5.85 (dd, 1H, J1=4.9 Hz, J2=8.4 Hz), 7.23 (s, 1H), 8.06 (s, 2H), 9.08 (br. s, 2H), 9.49 (d, 2H, J=8.4 Hz), 11.95 (s, 1H)

5. Example (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid

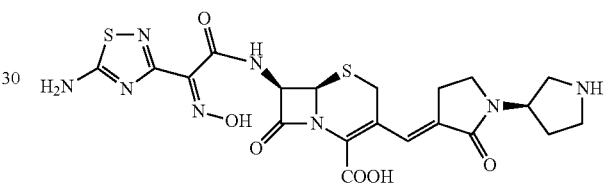

6.0 g of (6R,7R)-7-amino-3[E-(R)-1'-(5-tert-butyloxycarbonyl)-2-oxo-[1,3']bipyrrolidinyl-3-ylidenemethyl]-8-oxo-5-thia-1-aza-bicyclo[4.2.0]oct-2-ene-2-carboxylic acid in silylated form were dissolved in 300 ml of methylene chloride at 0°. 1,200 μl of DMF/water 5/1 and 8.1 ml of bis(tirmethylsilyl)acetamide were then added and 5.3 g of 2-trityloxyimino-2-(5-amino-1,2,4-thiadiazol-3-yl)-acetic acid chloride hydrochloride (J. Antibiotics 37:557-571, 1984) were metered into the mixture in portions. Thereafter, the mixture was poured onto 60 ml, of MeOH/240 ml of water and the methylene chloride phase was separated off. The organic phase was concentrated to 48 g and 1.5 ml of triethylsilane were added. After addition of 50 ml of trifluoroacetic acid, the mixture was stirred at room temperature for 60 min, 20 ml of water were added and the mixture was cooled to −15° C. The organic phase was separated off and washed once more with 20 ml of trifluoroacetic acid/water 1/1. The combined aqueous phases were diluted to 500 ml with water and treated with 2.0 g of active charcoal. After filtration, the solution was concentrated in vacuo.

The residue was diluted to 50 ml with water and the mixture was adjusted to pH 6.9 with saturated NaHCO$_3$ solution. The mixture was subsequently stirred at 0° C. for 2 h and the precipitate was washed with water.

Weight: 4.5 g $^1$H-nmr (DMSO-d$_6$/CF$_3$COOD) δ 1.9-2.3 (m, 2H), 2.8-3.5 (m, 8H), 3.85 (ABq, 2H, 18.7 Hz), 4.61 (m, 1H), 5.16 (d, 1H, J=4.8 Hz), 5.86 (dd, 1H, J1=4.8 Hz, J2=8.4 Hz), 7.24 (s, 1H), 8.05 (br s, 2H), 8.93 (s, 2H), 9.50 (d, 1H, J=8.4 Hz), 11.96 (s, 1H)

MS-ESI negative mode: 533.2 (M-H, 10%)

6. Example

Ceftobiprole Medocaril Na Salt

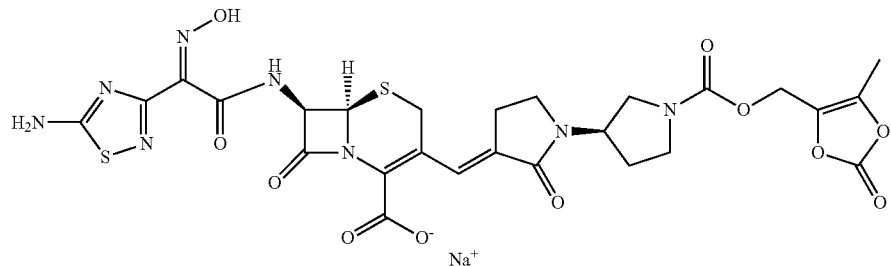 [SMILES: Cc1oc(=O)oc1COC(=O)N1CC[C@@H](N2CC/C(=C\C3=C(C(=O)[O-])N4C(=O)[C@@H](NC(=O)/C(=N\O)c5nsc(N)n5)[C@H]4SC3)C2=O)C1 ; [Na+]]

0.53 g of (6R,7R)-7-[(Z)-2-(5-amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid were dissolved in 5 ml of dimethylsulfoxide, 0.27 g of carbonic acid (5-methyl-2-oxo-[1,3]dioxol-4-ylmethyl)-4-nitrophenyl ester was added and the mixture was stirred at room temperature. For precipitation, a solution of sodium ethylhexanoate in 30 ml of acetone was added. The precipitate was filtered and washed with acetone.

Weight: 0.6 g $^1$H-nmr (DMSO-d$_6$) δ 1.9-2.05 (m, 2H), 2.10 (s, 3H), 2.7-3.1 (m, 2H), 3.1-3.6 (m, 6H), 3.64 (q, 2H; J=17.1 Hz), 4.56 (m, 1H), 4.87 (s, 2H), 4.98 (d, 1H, J=4.9 Hz), 5.65 (dd, 1H, J1=4.9 Hz, J2=8.4 Hz), 7.34 (s, 1H), 8.02 (s, 2H), 9.36 (d, 1H, J=8.4 Hz)

MS-ESI negative mode: 689.0 (M-H, 100%)

The invention claimed is:
1. A method for the production of a compound of the general formula (1)

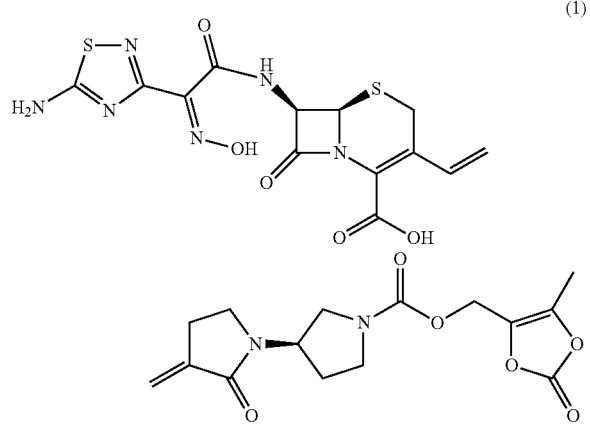

(1)

comprising the steps:
(a) reacting a compound of the formula (3)

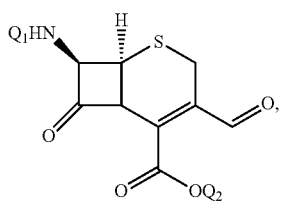

(3)

wherein $Q_1$ and $Q_2$ independently of each other represents a hydrogen atom or a silyl group, with a compound of the formula (4)

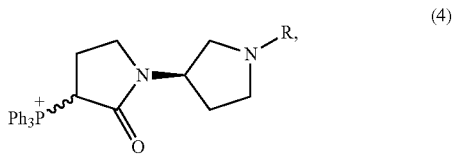

(4)

wherein R represents an amino-protective group, to produce a compound of the formula (5)

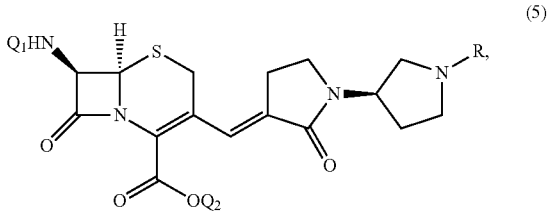

(5)

wherein $Q_1$, $Q_2$ and R are as defined above;
(b) reacting the compound of the formula (5) with a compound of the formula (6)

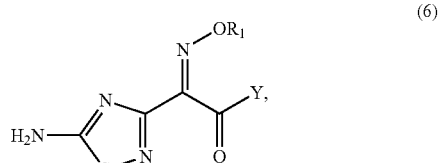

(6)

wherein $R_1$ represents a hydroxy-protective group and Y represents an activating functionality, wherein after optional removal of the protective group, if $Q_1$ represents a silyl group, to provide a compound of the formula (7)

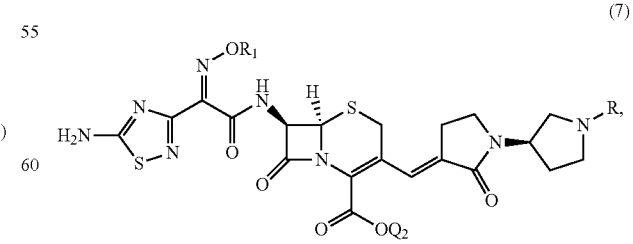

(7)

wherein $R_1$, $Q_2$ and R are as defined above;
converting the compound of the formula (7) into the compound of the formula (2) wherein for the reaction according to step (b) the compound of the formula (5) is dissolved by silylation or salt formation and step c) is carried out without intermediate isolation of the intermediate obtained from step b)

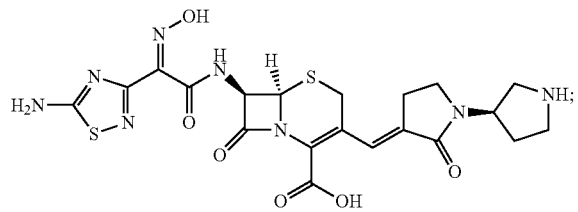
(2)

and (d) converting the compound of the formula (2) into a compound of the formula (1).

2. A method for the production of a compound of the formula (2)

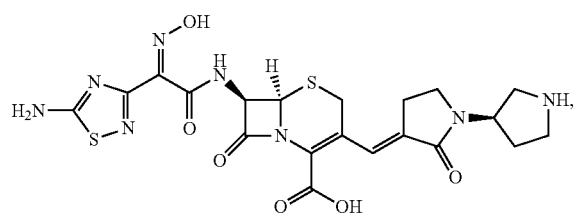
(2)

comprising at least the following steps (a), (b) and (c):

(a) reacting a compound of the formula (3)

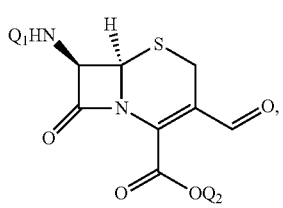
(3)

wherein $Q_1$ and $Q_2$ independently of each other represents a hydrogen atom or a silyl group, with a compound of the formula (4)

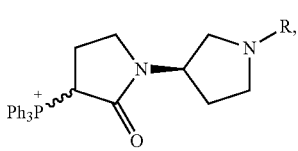
(4)

wherein R represents an amino-protective group, to produce a compound of the formula (5)

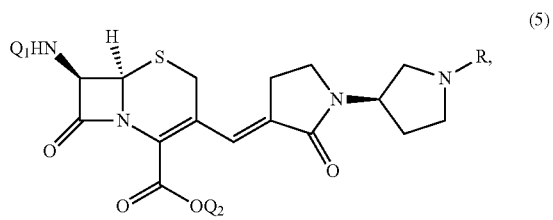
(5)

wherein $Q_1$, $Q_2$ and R are as defined above;

(b) reacting the compound of the formula (5) with a compound of the formula (6)

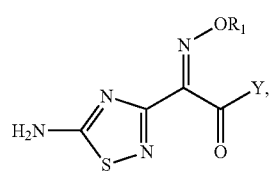
(6)

wherein $R_1$ represents a hydroxy-protective group and Y represents an activating functionality, wherein after optional removal of the protective group, if $Q_1$ represents a silyl group, to produce a compound of the formula (7)

(7)

wherein $R_1$, $Q_2$ and R are as defined above; and (c) converting the compound of the formula (7) into the compound of the formula (2), wherein for the reaction according to step (b) the compound of the formula (5) is dissolved by silylation or salt formation and step c) is carried out without intermediate isolation of the intermediate obtained from step b).

3. The method according to claim 1, wherein step (a) is carried out in the presence of a silylating agent and an epoxide.

4. The method according to claim 3, wherein the silylating agent is BSA.

5. The method according to claim 3, wherein the epoxide is propylene oxide.

6. The method according to claim 1, wherein the acylation with the compound of the formula (6) has been carried out, the protective groups are split off in one step.

7. The method according to claim 2, wherein step (a) is carried out in the presence of a silylating agent and an epoxide.

8. The method according to claim 7, wherein the silylating agent is BSA (N,O-Bis(trimethylsilyl)acetamide).

9. The method according to claim 7, wherein the epoxide is propylene oxide.

10. The method according to claim 2, wherein when the acylation with the compound of the general formula (6) has been carried out, the protective groups are split off in one step.

\* \* \* \* \*